(12) United States Patent
Chen et al.

(10) Patent No.: US 9,737,607 B2
(45) Date of Patent: Aug. 22, 2017

(54) POLYMER, AND PHARMACEUTICAL COMPOSITION EMPLOYING THE SAME

(71) Applicant: INDUSTRIAL TECHNOLOGY RESEARCH INSTITUTE, Hsinchu (TW)

(72) Inventors: Jui-Hsiang Chen, Hsinchu (TW);
Yu-Hua Chen, Hsinchu (TW);
Chia-Chen Tsai, Yunlin County (TW);
Tse-Min Teng, Hualien County (TW);
Ting-Yu Shih, Taipei (TW);
Chia-Chun Wang, Kaohsiung (TW);
Chia-wei Hong, Taoyuan (TW);
Jennline Sheu, Hsinchu (TW);
Hui-Ling Cheng, Hsinchu (TW);
Shu-Feng Chen, Hsinchu (TW);
Hung-Jui Huang, Kaohsiung (TW);
Shu-Ling Wang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 4 days.

(21) Appl. No.: 14/757,563

(22) Filed: Dec. 24, 2015

(65) Prior Publication Data

US 2016/0184437 A1 Jun. 30, 2016

(30) Foreign Application Priority Data

Dec. 24, 2014 (TW) .............................. 103145163 A

(51) Int. Cl.
*A61K 47/32* (2006.01)
*C08G 81/02* (2006.01)
(Continued)

(52) U.S. Cl.
CPC ............ *A61K 47/32* (2013.01); *A61K 9/1075* (2013.01); *A61K 31/18* (2013.01); *A61K 31/235* (2013.01);
(Continued)

(58) Field of Classification Search
CPC ...... A61K 31/235; A61K 47/32; A61K 9/146; C08G 18/283; C08G 18/755; C08G 81/021
See application file for complete search history.

(56) References Cited

U.S. PATENT DOCUMENTS 3,984,494 A 10/1976 Harréus et al.
4,540,743 A 9/1985 Schulz et al.
(Continued)

FOREIGN PATENT DOCUMENTS

CN 1863515 A 11/2006
CN 10146014 B 11/2012
(Continued)

OTHER PUBLICATIONS

Brüggemann et al., "Comparison of polymer coatings of capillaries for capillary electrophoresis with respect to their applicability to molecular imprinting and electrochromatography," Journal of Chromatography A, vol. 781, 1997, pp. 43-53.
(Continued)

*Primary Examiner* — Timothy Thomas
*Assistant Examiner* — Andrew S Rosenthal
(74) *Attorney, Agent, or Firm* — Birch, Stewart, Kolasch & Birch, LLP

(57) ABSTRACT

A polymer and a pharmaceutical composition employing the same are disclosed. The polymer includes a first repeating unit, a second repeating unit, and a third repeating unit. In particular, the first repeating unit is

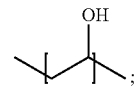

the second repeating unit is

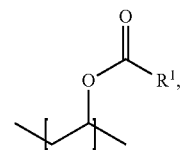

wherein $R^1$ is $C_{1-6}$ alkyl group; and the third repeating unit is wherein X is (Continued)

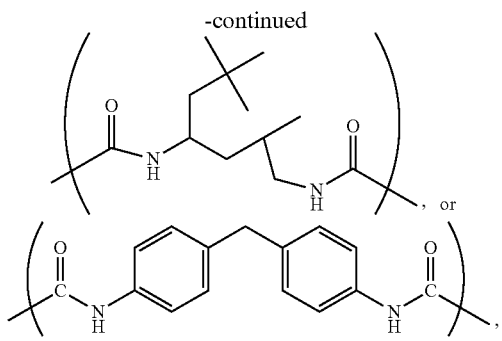

, or and Y is a hydrophilic polymeric moiety.

19 Claims, 5 Drawing Sheets

(51) Int. Cl.

| | | |
|---|---|---|
| *A61K 9/107* | (2006.01) | |
| *A61K 31/18* | (2006.01) | |
| *A61K 31/235* | (2006.01) | |
| *A61K 31/437* | (2006.01) | |
| *A61K 31/44* | (2006.01) | |
| *A61K 31/5377* | (2006.01) | |
| *A61K 31/551* | (2006.01) | |
| *A61K 38/07* | (2006.01) | |
| *C08G 18/62* | (2006.01) | |
| *C08G 18/71* | (2006.01) | |
| *C08G 18/73* | (2006.01) | |
| *C08G 18/75* | (2006.01) | |
| *C08G 18/76* | (2006.01) | |
| *C08G 18/80* | (2006.01) | |
| *C08G 18/28* | (2006.01) | |
| *A61K 9/14* | (2006.01) | |
| *A61K 9/20* | (2006.01) | |

(52) U.S. Cl.
CPC ............ *A61K 31/437* (2013.01); *A61K 31/44* (2013.01); *A61K 31/5377* (2013.01); *A61K 31/551* (2013.01); *A61K 38/07* (2013.01); *C08G 18/283* (2013.01); *C08G 18/6212* (2013.01); *C08G 18/711* (2013.01); *C08G 18/73* (2013.01); *C08G 18/755* (2013.01); *C08G 18/7671* (2013.01); *C08G 18/8064* (2013.01); *C08G 81/021* (2013.01); *C08G 81/025* (2013.01); *C08G 81/027* (2013.01); *A61K 9/146* (2013.01); *A61K 9/2027* (2013.01)

(56) References Cited

U.S. PATENT DOCUMENTS

| | | |
|---|---|---|
| 4,746,456 A | 5/1988 | Kud et al. |
| 8,198,364 B2 | 6/2012 | Zhu et al. |
| 8,216,495 B2 | 7/2012 | Janssens et al. |
| 8,460,692 B2 | 6/2013 | Zhang et al. |
| 2009/0087486 A1 | 4/2009 | Krumme |
| 2014/0010872 A1 | 1/2014 | Kim et al. |

FOREIGN PATENT DOCUMENTS

| | | | |
|---|---|---|---|
| CN | EP 2604645 A1 * | 6/2013 | ......... C08G 18/4833 |
| EP | 2 604 645 A1 | 6/2013 | |
| TW | 200940069 A1 | 10/2009 | |
| TW | 201323026 A1 | 6/2010 | |
| TW | 201328727 A1 | 7/2013 | |
| WO | WO 2007/115381 A2 | 10/2007 | |

OTHER PUBLICATIONS

Guns et al., "Comparison Between Hot-Melt Extrusion and Spray-Drying for Manufacturing Solid Dispersions of the Graft Copolymer of Ethylene Glycol and Vinylalcohol," Pharmaceutical Research, vol. 28, 2011 (published online Nov. 23, 2010), pp. 673-682.
Luo et al., "Poly(vinyl alcohol)—graft-poly(ethylene glycol) resins and their use in solid-phase synthesis and supported TEMPO catalysis," Chemical Communications, Supplementary Material, 2007, pp. S1-S8.
Luo et al., "Preparation, Characterization, and Application of Poly(vinyl alcohol)-graft-Poly(ethylene glycol) Resins: Novel Polymer Matrices for Solid-Phase Synthesis," Journal of Combinatorial Chemistry, vol. 9, No. 4, 2007, pp. 582-591.
Zhang et al., "Preparation and Properties of Polymeric Solid-solid Phase Change Materials of Polyethylene Glycol (PEG)/Poly(vinyl alcohol) (PVA) Copolymers by Graft Copolymerization," Chemical Journal of of Chinese Universities, vol. 26, No. 1, Jan. 2005, pp. 170-174.
Extended European Search Report, dated May 13, 2016, for corresponding European Application No. 15202204.2.
Llanos et al., "Immobilization of Poly(ethylene glycol) onto a Poly(vinyl alcohol) Hydrogel. 1. Synthesis and Characterization," Macromolecules, vol. 24, No. 23, 1991 (Nov. 30, 1991), pp. 6065-6072.

* cited by examiner

POLYMER, AND PHARMACEUTICAL COMPOSITION EMPLOYING THE SAME

CROSS REFERENCE TO RELATED APPLICATIONS

The application is based on, and claims priority from, Taiwan Application Serial Number 103145163, filed on Dec. 24, 2014, the disclosure of which is hereby incorporated by reference herein in its entirety.

TECHNICAL FIELD

The disclosure relates to a polymer and a pharmaceutical composition employing the same.

BACKGROUND

The Biopharmaceutical Classification System (BCS), originally developed by G. Amidon, separates pharmaceuticals for oral administration into four classes depending on their solubility and their absorbability:
  Class I—High Permeability, High Solubility
  Class II—High Permeability, Low Solubility
  Class III—Low Permeability, High Solubility
  Class IV—Low Permeability, Low Solubility Due to the hydrophobic and lipophilic characteristics, the compounds classified as BCS Class II are apt to appear to have spontaneous self-aggregation when mixed with water, resulting in the development of pharmaceutical formulations employing the compound classified as BCS Class II being very limited. However, about 70% of clinically developed drugs are classified as BCS Class II. In order to achieve the expected effect of drugs, the solubility of drugs should be improved to force the dissolved drug into single-molecule form.

Therefore, it is crucial to improve the solubility, absorption, and dissolution of the compounds classified as BCS Class II within the human body, in order to enhance the bio-availability of drugs.

SUMMARY

According to embodiments of the disclosure, the disclosure provides a polymer. The polymer includes a first repeating unit, a second repeating unit, and a third repeating unit, wherein the first repeating unit is

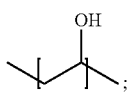

the second repeating unit is

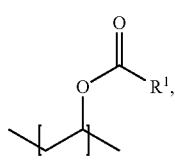

wherein R¹ is C_{1-6} alkyl group; and, the third repeating unit is

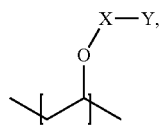

wherein X is

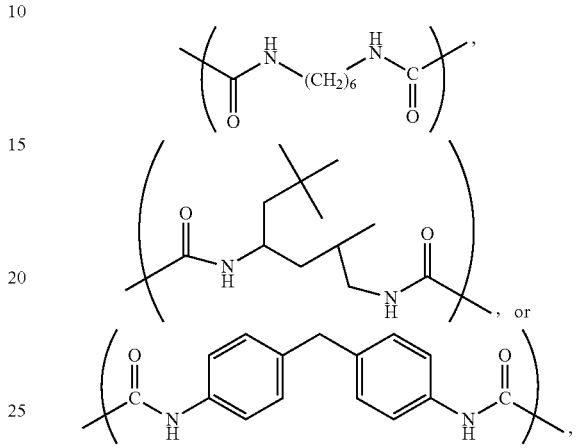

and Y is hydrophilic polymeric moiety.

According to another embodiment of the disclosure, the disclosure also provides a pharmaceutical composition including the aforementioned polymer serving as an excipient. The pharmaceutical composition includes a bioactive component; and an excipient, wherein the excipient includes the aforementioned polymer.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

FIG. 2 is a graph plotting the solubility of the modified polyvinyl alcohol (2), (3), and (9) prepared from Examples 2, 3, and 9 and the excipient HPMC-AS.

FIG. 3 is a graph plotting the solubility of the modified polyvinyl alcohol (3)-(5), and (8)-(12) prepared from Examples 3-5 and 8-12 and HPMC-AS.

FIG. 5 is a graph plotting the cell viability of the modified polyvinyl alcohol (1), (2), (3), (5), (8), (9), and (12) prepared from Examples 1, 2, 3, 5, 8, 9, and 12, the commercially available excipient Kollidon® VA64 and HPMC-AS.

DETAILED DESCRIPTION

Figure 1:
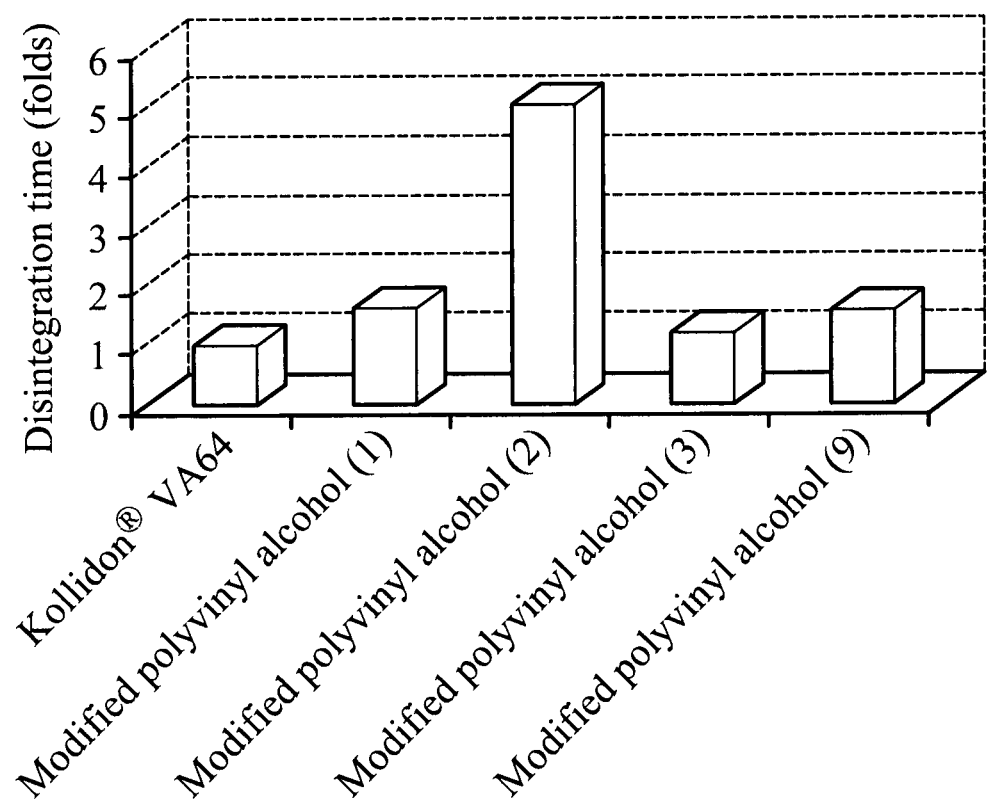
FIG. 1 is a graph plotting the disintegration time of the modified polyvinyl alcohol (1), (2), (3), and (9) prepared from Examples 1, 2, 3, and 9 and the commercially available excipient Kollidon® VA64.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The disclosure provides a polymer, and pharmaceutical composition employing the same. The polymer is a modified polyvinyl alcohol, wherein the hydroxy group of polyvinyl alcohol is modified by hydrophilic polymeric moiety, and alkanoyl group. In addition, according to embodiments of the disclosure, the polymer of the disclosure can be a modified polyvinyl alcohol, wherein the hydroxy group of polyvinyl alcohol is modified by hydrophilic polymeric moiety, alkanoyl group, and hydrophobic moiety. Due to the solubility of the polymer, the polymer of the disclosure can serve as an excipient for improving the absorption, and dissolution of the compounds classified as BCS Class II within the human body. As a result, the bio-availability of the drugs can be enhanced by means of the polymer, without changing the dosage form of the drugs. The polymer would appear to spontaneously have a micelle structure when mixed with water. The hydrophobic part of the core of the micelle structure can encapsulate the insoluble drug, and the hydrophilic part can ensure that the micelle structure disperses stably and uniformly in water and reduces the accumulation of drugs. The polymer of the disclosure serving as an excipient can improve the solubility and avoid the accumulation of the compounds classified as BCS Class II, the bio-availability of the drugs can be enhanced. On the other hand, by means of the polymer of the disclosure exhibiting solubility and having the functions for disintegrating and/or bonding the pharmaceutical composition, the amount of the additional excipient used in a solid dosage form of the pharmaceutical composition can be reduced, resulting in the reduction of side reaction of drugs.

The polymer of the disclosure can include a first repeating unit, a second repeating unit, and a third repeating unit, wherein the first repeating unit, the second repeating unit, and the third repeating unit are arranged in a random fashion. The first repeating unit can be

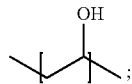

the second repeating unit can be

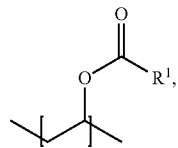

wherein $R^1$ is $C_{1-6}$ alkyl group; and, the third repeating unit can be

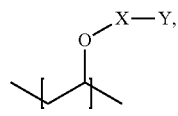

wherein X is

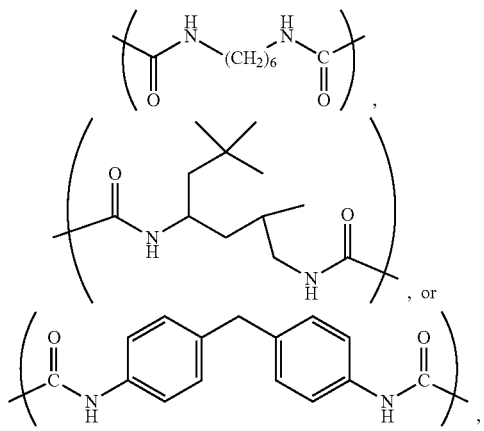

and Y is hydrophilic polymeric moiety.

According to embodiments of the disclosure, the hydrophilic polymeric moiety can be polyethylene glycol (PEG) moiety, methoxy polyethylene glycol (mPEG) moiety, polyvinylpyrrolidone (PVP) moiety, polyacrylic acid (PAA) moiety, or polymethacrylic acid (PMA) moiety. The hydrophilic polymeric moiety has a weight average molecular weight between about 500 and 100,000, such between about 1,000 and 80,000, or between about 1,500 and 60,000. The stability of the micelle and the state of the polymer can be improved by adjusting the molecular weight (such as weight average molecular weight) of the hydrophilic polymeric moiety. According to embodiments of the disclosure, the hydrophilic polymeric moiety can be polyethylene glycol (polyethylene glycol, PEG) moiety, or methoxy polyethylene glycol moiety, wherein the polyethylene glycol moiety (or methoxy polyethylene glycol moiety) is bonded with the X moiety via the residual group eliminating hydrogen atom from terminal hydroxyl group. Namely, the third repeating unit can be

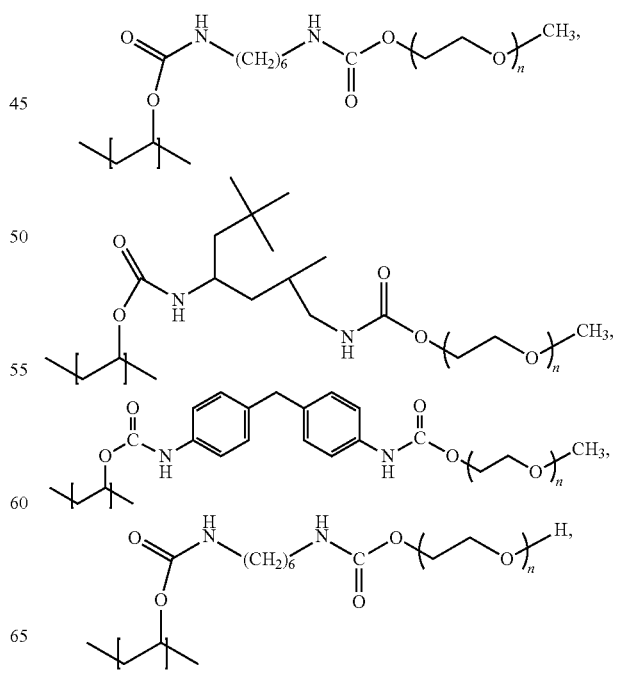

-continued

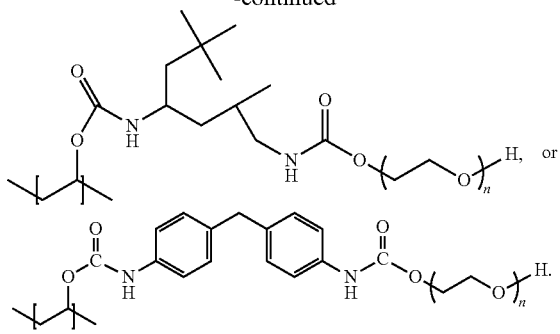

According to embodiments of the disclosure, the hydrophilic polymeric moiety has a grafting ratio between about 0.1% and 10%, such as between about 1% and 8%. The hydrophilic polymeric moiety grafting ratio of the polymer is determined by measuring the percentage of the third repeating unit, based on the total of the first, second, and third repeating units. When the hydrophilic polymeric moiety grafting ratio is too low, the polymer is not apt to form micelle and insoluble in water, resulting in reduction of solubility. When the hydrophilic polymeric moiety grafting ratio is too low, the drug loading of the polymer is reduced, resulting in reduction of solubility.

According to embodiments of the disclosure, R1 of the second repeating unit can be methyl group, ethyl group, propyl group, isopropyl group, butyl group, isobutyl group, tert-butyl group, pentyl group, or hexyl group. For example, the second repeating unit can be

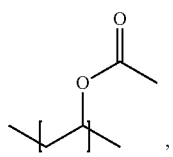

and the polymer has an esterification degree between 10% and 85%, wherein the esterification degree of the polymer is determined by measuring the percentage of the second repeating unit, based on the total of the first, second, and third repeating units.

According to embodiments of the disclosure, the polymer of the disclosure has a weight average molecular weight between about 5,000 and 500,000, such as between about 8,000 and 400,000, or between about 8,000 and 300,000. The molecular weight of the polymer can be adjusted according to the lipophilicity of the drug, in order to increase the solubility.

According to embodiments of the disclosure, the first repeating unit of the polymer has a weight percentage between about 5 wt %-50 wt %, the second repeating unit has a weight percentage between about 10 wt %-55 wt %, and the third repeating unit has a weight percentage between about 25 wt %-75 wt %, wherein the weight percentage is based on the total weight of the first repeating unit, the second repeating unit, and the third repeating unit. When the weight percentage of the first repeating unit (or the third repeating unit) is too low or the weight percentage of the second repeating unit is too high, the polymer has lower solubility in water (the solubility would be improved by mixing with organic solvent) and is not apt to form micelle due to the increased hydrophobicity, resulting in reduction of solubility. When the weight percentage of the first repeating unit (or the third repeating unit) is too high or the weight percentage of the second repeating unit is too low, the micelle of the polymer in water is unstable due to the increased hydrophilicity, resulting in not being able to use the polymer to encapsulate hydrophobic drugs. In addition, according to other embodiments of the disclosure, the first repeating unit has a weight percentage between about 10 wt %-45 wt %, the second repeating unit has a weight percentage between about 15 wt %-50 wt %, and the third repeating unit has a weight percentage between about 25 wt %-70 wt %.

According to embodiments of the disclosure, the polymer can further include a fourth repeating unit, wherein the fourth repeating unit is

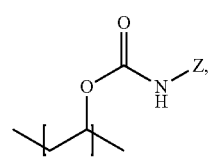

wherein Z is a hydrophobic moiety. The first repeating unit, second repeating unit, third repeating unit, and the fourth repeating unit are arranged in a random fashion. The hydrophobic moiety can be phenyl group, naphthyl group, or $C_{4-20}$ alkyl group (such as: —$C_5H_{11}$, —$C_7H_{15}$, —$C_9H_{19}$, or —$C_{11}H_{23}$). In addition, According to other embodiments of the disclosure, the hydrophobic moiety can be polyester moiety, such as: polycaprolactone moiety, polylactic acid moiety, polyglycolic acid moiety, or poly(lactic-co-glycolic) acid moiety, wherein, the polyester moiety can have a weight average molecular weight between 500 and 5,000.

According to embodiments of the disclosure, the first repeating unit of the polymer of the disclosure has a weight percentage between about 5 wt %-40 wt %, the second repeating unit has a weight percentage between about 10 wt %-50 wt %, the third repeating unit has a weight percentage between about 25 wt %-70 wt %, and the fourth repeating unit has a weight percentage between about 5 wt %-50 wt %, wherein the weight percentage is based on the total weight of the first repeating unit, the second repeating unit, the third repeating unit, and fourth repeating unit. According to some embodiments of the disclosure, the hydrophobic moiety has a grafting ratio between about 0.1% and 10%, such as between about 1% and 8%. The hydrophobic polymeric moiety grafting ratio of the polymer is determined by measuring the percentage of the fourth repeating unit, based on the total of the first, second, third and fourth repeating units. When the hydrophobic polymeric moiety grafting ratio is too high, the polymer has lower solubility in water (the solubility would be improved by mixing with organic solvent) and is not apt to form micelle due to the increased hydrophobicity, resulting in reduction of solubility. When the hydrophobic polymeric moiety grafting ratio is too low, the drug loading of the polymer is reduced, resulting in reduction of solubility. Further, the micelle of the polymer in water is unstable due to the increased hydrophilicity, resulting in the polymer being unable to encapsulate hydrophobic drugs. The hydrophobic of the polymer can be adjusted according to the drug, which is encapsulated by the polymer, in order to enhance the solubility of the drugs.

The esterification, hydrophilic moiety grafting, and hydrophobic moiety grafting for preparing the polymer of the disclosure does not have to be performed in a particular order. In Examples of the disclosure, the esterification, hydrophilic moiety grafting, and hydrophobic moiety grafting for preparing the polymer performed in that order are merely illustrative.

The disclosure provides a pharmaceutical composition, including a bioactive component, and an excipient, wherein the excipient includes the aforementioned polymer. The weight ratio between the bioactive component and the excipient is between about 10:1 and 1:20. According to embodiments of the disclosure, since the polymer of the disclosure exhibits superior binding capacity and sustained capability, the pharmaceutical composition can be in the form of tablets, capsules, powders, flakes, powders, microcapsules, suspensions, emulsions, or granules. In addition, the bioactive component can be nanoparticles, microcapsules, liposomes, micelles, emulsions and the like.

According to embodiments of the disclosure, due to the solubility, the polymer of the disclosure can serve as an excipient for improving the absorption and dissolution of the compounds classified as BCS Class II. Therefore, the bioavailability of the drugs can be enhanced by means of the polymer, without changing the dosage form of the drugs. The bioactive component can be lipophilic drugs. In addition, the bioactive component can be non-steroid anti-inflammatory drugs, psychotropic drugs, antilipemic drugs, antiemetic drugs, or a combination thereof. According to other embodiments of the disclosure, the bioactive component can be salicylic acid derivative, propionic acid derivative, phenylacetic acids derivative, indoleacetic acids) derivative, oxicams derivative, or pyrazalones derivative, such as ibuprofen, naproxen, ketoprofen, flurbiprofen, fenoprofen, suprofen, fluprofen, fenbufen, tolmetin sodium, zomepirac, sulindac, indomethacin, mefenamic acid, meclofenamate, diflunisal, flufenisal, piroxicam, sudoxicam, isoxicam, chlorpheniramine, brompheniramine, dexchlorpheniramine, dexbrompheniramine, triprolidine, chlorcyclizine, diphenhydramine, doxylamine, tripelennamine, cyproheptadine, bromodiphenhydramin, phenindamine, pyrilamine, azatadine, acrivastine, astemizole, azelastine, cetirizine, ebastine, fexofenadine, ketotifen, carbinoxamine, desloratadine, loratadine, pheniramine, thonzylamine, mizolastine, terfenadine, chlophendianol, caramiphen, dextromethorphan, codeine, hydrocodone, pseudoephedrine, ephedrine, phenylephrine, guaifenesin, guaiacotsulfonate, celecoxib, rofecoxib, valdecoxib, acetaminophen, phenacetin, acteylsalicylic acid, aripiprazole, fenofibrate, aprepitant, nevirapine, glyburide, sorafenib, vemurafenib, telaprevir, or a combination thereof.

The following examples are intended to illustrate the disclosure more fully without limiting the scope, since numerous modifications and variations will be apparent to those skilled in this art.

PREPARATION EXAMPLE 1

First, polyvinyl acetate (PVAc) with esterification degree of 20% (having a weight average molecular weight between about 10,000-12,000) (1 eq) was disposed into a reaction bottle, and then dried under vacuum at 60° C. for 24 hr. Next, the polyvinyl acetate was dissolved in dimethylacetamide (DMAc), and then stirred and heated to 80° C. for 2 hr. Next, the reaction bottle was cooled to room temperature, and 4-dimethylaminopyridine (DMAP) was added into the reaction bottle (0.01 eq). After stirring for 10 min, the reaction bottle was placed in a water bath tank at room temperature, and then acetic anhydride (0.2 eq) was added slowly into the reaction bottle. After the addition of acetic anhydride is complete, triethylamine (0.22 eq) was added into the reaction bottle at room temperature and stirred at 40° C. for 16 hr. Next, after cooling to room temperature, a substantial amount of ethyl ether was added into the reaction bottle. After stirring for 1 hr and then standing, the precipitate was gathered. The above step was repeated two more times, and then the precipitate was dried under vacuum, obtaining polyvinyl acetate (white solid). Next, $^1$H-NMR spectrum of obtained compound was measured, and the esterification degree polyvinyl acetate was determined (according to the area integrations of —CH$_3$ peak (δ=2.0-1.8) and —CH$_2$ peak (δ=1.2-1.8). The result was shown in Table 1.

PREPARATION EXAMPLE 2

Preparation Example 2 was performed in the same manner as in Preparation Example 1 except that 0.01 eq of 4-dimethylaminopyridine (DMAP) was substituted with 0.02 eq of 4-dimethylaminopyridine, 0.2 eq of acetic anhydride was substituted with 0.4 eq of acetic anhydride, and 0.22 eq of trimethylamine was substituted with 0.44 eq of trimethylamine. Next, the esterification degree of the polyvinyl acetate obtained from Preparation Example 2 was determined, and the result was shown in Table 1.

PREPARATION EXAMPLE 3

Preparation Example 3 was performed in the same manner as in Preparation Example 1 except that 0.01 eq of 4-dimethylaminopyridine (DMAP) was substituted with 0.03 eq of 4-dimethylaminopyridine, 0.2 eq of acetic anhydride was substituted with 0.6 eq of acetic anhydride, and 0.22 eq of trimethylamine was substituted with 0.66 eq of trimethylamine. Next, the esterification degree of the polyvinyl acetate obtained from Preparation Example 3 was determined, and the result was shown in Table 1.

TABLE 1

| | components (eq) | | | | |
|---|---|---|---|---|---|
| | polyvinyl acetate (esterification degree 20%) | acetic anhydride | DMAP | triethyl-amine | esterification degree of polyvinyl acetate (%) |
| Preparation Example 1 | 1 | 0.2 | 0.01 | 0.22 | 36 |
| Preparation Example 2 | 1 | 0.4 | 0.02 | 0.44 | 62 |
| Preparation Example 3 | 1 | 0.6 | 0.03 | 0.66 | 77 |

PREPARATION EXAMPLE 4

19.0 g of methoxy polyethylene glycol (having a weight average Molecular weight of 1900) was added into a reaction bottle, and then dried in a vacuum oven at 100° C. for 24 hr. After cooling to room temperature, 47.9 mL of dimethyl sulfoxide (DMSO) was added into the reaction bottle in nitrogen atmosphere, and heated to 60-70° C. to force the methoxy polyethylene glycol completely dissolved in DMSO. After cooling to room temperature, 1.5 g of hexamethylene diisocyanate (HDI) was added into the reaction bottle, and heated to 90° C. to react without the addition of catalyst. Next, the reaction was terminated after being checked the weight average molecular weight of product by gel permeation chromatography, obtaining active methoxy polyethylene glycol prepolymer (1) (with a structure of

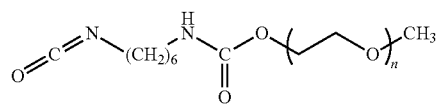

(n>1))(having a weight average molecular weight of 1700-2200). The synthesis pathway of the above reaction was as follows:

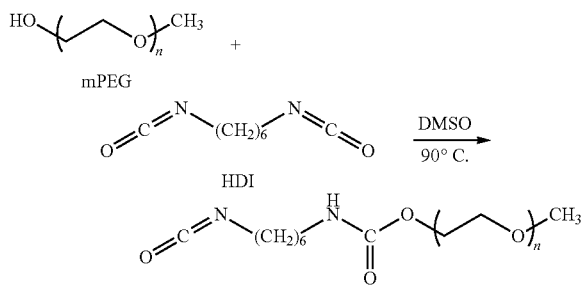

PREPARATION EXAMPLE 5

Preparation Example 5 was performed in the same manner as in Preparation Example 4 except that 19.0 g of methoxy polyethylene glycol (with a weight average molecular weight of 1900) was substituted with 20.0 g of methoxy polyethylene glycol (with a weight average molecular weight of 2000), obtaining active methoxy polyethylene glycol prepolymer (2).

PREPARATION EXAMPLE 6

Preparation Example 6 was performed in the same manner as in Preparation Example 4 except that 19.0 g of methoxy polyethylene glycol (with a weight average molecular weight of 1900) was substituted with 25.0 g of methoxy polyethylene glycol (with a weight average molecular weight of 5000), obtaining active methoxy polyethylene glycol prepolymer (3).

PREPARATION EXAMPLE 7

25.0 g of methoxy polyethylene glycol (with a weight average Molecular weight 2000) was added into a reaction bottle, and dried in a vacuum oven at 100° C. for 24 hr. After cooling to room temperature, 53 mL of dimethyl sulfoxide (DMSO) was added into the reaction bottle in nitrogen atmosphere, and heated to 60-70° C. to force the methoxy polyethylene glycol completely dissolved in DMSO. After cooling to room temperature, 2.8 g of methylene diphenyl diisocyanate (MDI) was added into the reaction bottle, and heated to 50° C. to react without the addition of catalyst. Next, the reaction was terminated after being checked the weight average molecular weight of product by gel permeation chromatography, obtaining active methoxy polyethylene glycol prepolymer (4) (with a structure of

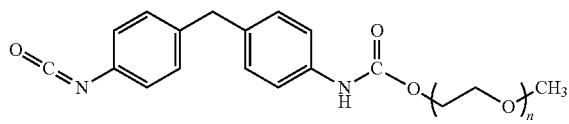

(n>1))(having a weight average molecular weight of 1700-2200). The synthesis pathway of the above reaction was as follows:

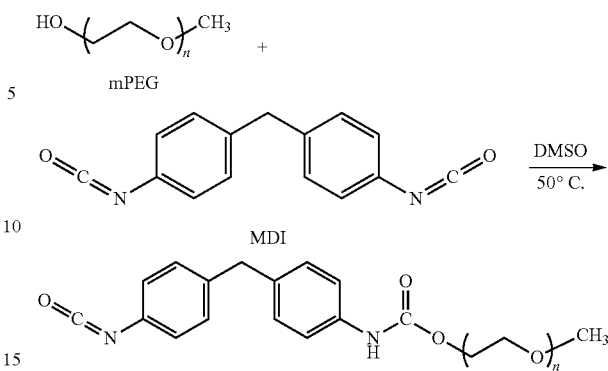

PREPARATION EXAMPLE 8

190 g of methoxy polyethylene glycol (with a weight average molecular weight 2000) was added into a reaction bottle, and dried in a vacuum oven at 100° C. for 24 hr. After cooling to room temperature, 490 mL of dimethyl sulfoxide (DMSO) was added into the reaction bottle in nitrogen atmosphere, and heated to 60-70° C. to force the methoxy polyethylene glycol completely dissolved in DMSO. After cooling to room temperature, 20 g of isophorone diisocyanate (IPDI) was added into the reaction bottle, and heated to 80° C. to react without the addition of catalyst. Next, the reaction was terminated after being checked the weight average molecular weight of product by gel permeation chromatography, obtaining active methoxy polyethylene glycol prepolymer (5) (with a structure of

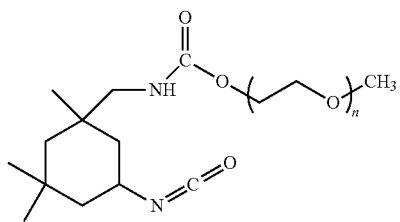

(n>1))(having a weight average molecular weight of 1700-2200). The synthesis pathway of the above reaction was as follows:

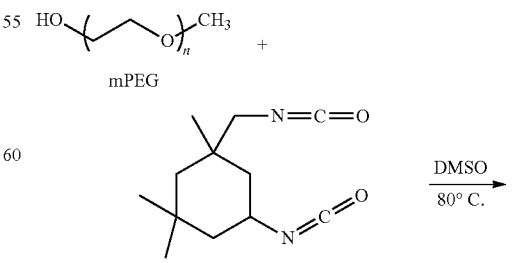

-continued

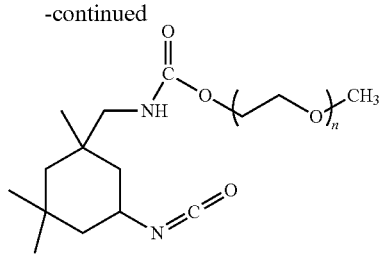

Preparation of Modified polyvinyl alcohol

EXAMPLE 1

Methoxy polyethylene glycol prepolymer (1) (prepared according to Preparation Example 4, and the amount of methoxy polyethylene glycol prepolymer (with a weight average molecular weight of about 1900) and hexamethylene diisocyanate (HDI) are shown in Table 2), 15.8 g of polyvinyl acetate (with a weight average molecular weight of about 10,000-12,000) (having an esterification degree of 20%), and 170 mL of dimethyl sulfoxide (DMSO) were added into a reaction bottle. After stirring uniformly, the reaction bottle was heated to 90° C. After reacting for 16 hr, the reaction bottle was cooled to room temperature, and a substantial amount of ethyl ether was added into the reaction bottle. After stirring for 1 hr and then standing, the precipitate was gathered. Next, the precipitate was dried in a vacuum oven at 80° C. Next, the result was extracted using dichloromethane as the extraction solvent, obtaining the modified polyvinyl alcohol (1) (having the repeating unit A

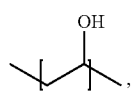

repeating unit B

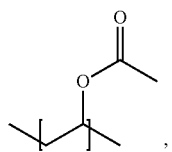

and repeating unit C

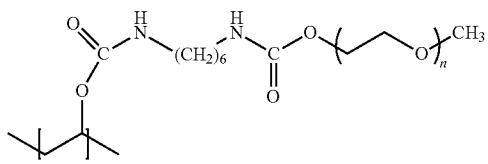

(n>1, and the moiety

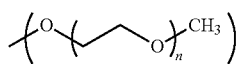

having a weight average molecular weight of about 1900), wherein the repeating units A, B, and C are arranged in a random fashion).

EXAMPLE 2

Example 2 was performed in the same manner as in Example 1 except that the amounts of methoxy polyethylene glycol and hexamethylene diisocyanate (HDI) using for preparing methoxy polyethylene glycol prepolymer (1) shown in Table 2 were used instead of those disclosed in Example 1, 15.8 g of polyvinyl acetate (PVAc) (having an esterification degree of 20%) was substituted with 86.2 g of polyvinyl acetate (PVAc) (having an esterification degree of 20%), and 170 mL of dimethyl sulfoxide (DMSO) was substituted with 713 mL of dimethyl sulfoxide (DMSO), obtaining modified polyvinyl alcohol (2) (having the repeating unit A

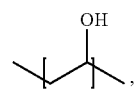

repeating unit B

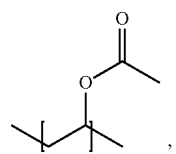

and repeating unit C

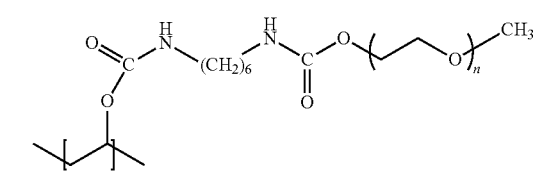

and the moiety

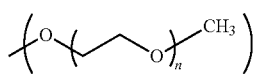

having a weight average molecular weight of about 1900), wherein the repeating units A, B, and C are arranged in a random fashion).

EXAMPLE 3

Example 3 was performed in the same manner as in Example 1 except that the amounts of methoxy polyethylene glycol and hexamethylene diisocyanate (HDI) using for preparing methoxy polyethylene glycol prepolymer (1) shown in Table 2 were used instead of those disclosed in Example 1, 15.8 g of polyvinyl acetate (PVAc) (having an esterification degree of 20%) was substituted with 137.9 g of polyvinyl acetate (PVAc) (having an esterification degree of 20%), and 170 mL of dimethyl sulfoxide (DMSO) was substituted with 716 mL of dimethyl sulfoxide (DMSO), obtaining modified polyvinyl alcohol (3) (having the repeating unit A

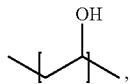

repeating unit B

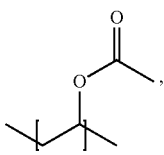

and repeating unit C

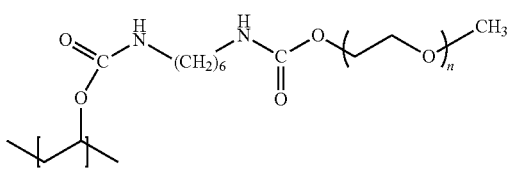

($n>1$, and the moiety

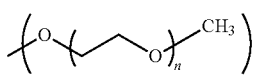

having a weight average molecular weight of about 1900), wherein the repeating units A, B, and C are arranged in a random fashion).

EXAMPLE 4

Example 4 was performed in the same manner as in Example 1 except that the amounts of methoxy polyethylene glycol and hexamethylene diisocyanate (HDI) using for preparing methoxy polyethylene glycol prepolymer (1) shown in Table 2 were used instead of those disclosed in Example 1, 15.8 g of polyvinyl acetate (PVAc) (having an esterification degree of 20%) was substituted with 46 g of polyvinyl acetate (PVAc) (having an esterification degree of 20%), and 170 mL of dimethyl sulfoxide (DMSO) was substituted with 611 mL of dimethyl sulfoxide (DMSO), obtaining modified polyvinyl alcohol (4) (having the repeating unit A

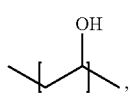

repeating unit B

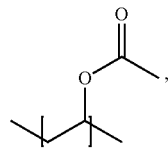

and repeating unit C

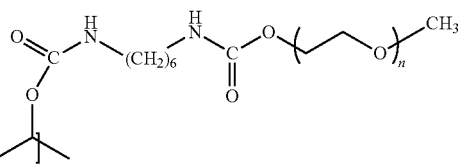

($n>1$, and the moiety

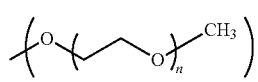

having a weight average molecular weight of about 1900), wherein the repeating units A, B, and C are arranged in a random fashion).

EXAMPLE 5

Example 5 was performed in the same manner as in Example 1 except that the amounts of methoxy polyethylene glycol and hexamethylene diisocyanate (HDI) using for preparing methoxy polyethylene glycol prepolymer (1) shown in Table 2 were used instead of those disclosed in Example 1, 15.8 g of polyvinyl acetate (PVAc) (having an esterification degree of 20%) was substituted with 124.1 g of polyvinyl acetate (PVAc) (having an esterification degree of 20%), and 170 mL of dimethyl sulfoxide (DMSO) was substituted with 847 mL of dimethyl sulfoxide (DMSO), obtaining modified polyvinyl alcohol (5) (having the repeating unit A,

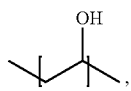

repeating unit B

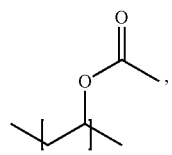

and repeating unit C

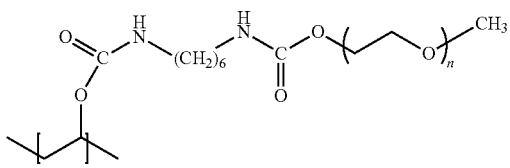

(n>1, and the moiety

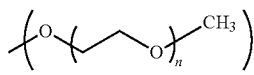

having a weight average molecular weight of about 1900), wherein the repeating units A, B, and C are arranged in a random fashion).

EXAMPLE 6

Example 6 was performed in the same manner as in Example 1 except that the amounts of methoxy polyethylene glycol and hexamethylene diisocyanate (HDI) using for preparing methoxy polyethylene glycol prepolymer (1) shown in Table 2 were used instead of those disclosed in Example 1, 15.8 g of polyvinyl acetate (PVAc) (having an esterification degree of 20%) was substituted with 137.9 g of polyvinyl acetate (PVAc) (having an esterification degree of 20%), and 170 mL of dimethyl sulfoxide (DMSO) was substituted with 716 mL of dimethyl sulfoxide (DMSO), obtaining modified polyvinyl alcohol (6) (having the repeating unit A

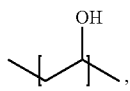

repeating unit B

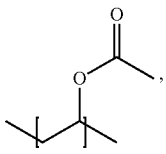

and repeating unit C

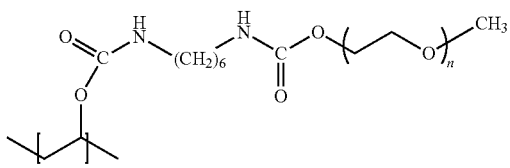

(n>1, and the moiety

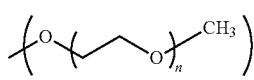

having a weight average molecular weight of about 1900), wherein the repeating units A, B, and C are arranged in a random fashion).

EXAMPLE 7

Methoxy polyethylene glycol prepolymer (2) (prepared according to Preparation Example 5, and the amount of methoxy polyethylene glycol prepolymer (with a weight average molecular weight of about 2000) and hexamethylene diisocyanate (HDI) are shown in Table 2), 86.2 g of polyvinyl acetate (with a weight average molecular weight of about 10,000-12,000) (having an esterification degree of 20%), and 740 mL of dimethyl sulfoxide (DMSO) were added into a reaction bottle. After stirring uniformly, the reaction bottle was heated to 90° C. After reacting for 16 hr, the reaction bottle was cooled to room temperature, and a substantial amount of ethyl ether was added into the reaction bottle. After stirring for 1 hr and then standing, the precipitate was gathered. Next, the precipitate was dried in a vacuum oven at 80° C. Next, the result was extracted using dichloromethane as the extraction solvent, obtaining the modified polyvinyl alcohol (7) (having the repeating unit A

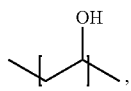

repeating unit B

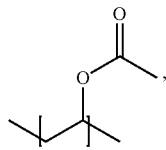

and repeating unit C

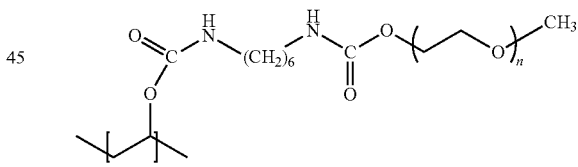

(n>1, and the moiety

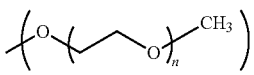

having a weight average molecular weight of about 2000), wherein the repeating units A, B, and C are arranged in a random fashion).

EXAMPLE 8

Methoxy polyethylene glycol prepolymer (3) (prepared according to Preparation Example 6, and the amount of methoxy polyethylene glycol prepolymer (with a weight average molecular weight of about 5000) and hexamethylene diisocyanate (HDI) are shown in Table 2), 78.6 g of polyvinyl acetate (with a weight average molecular weight of about 10,000-12,000) (having an esterification degree of 20%), and 485 mL of dimethyl sulfoxide (DMSO) were added into a reaction bottle. After stirring uniformly, the reaction bottle was heated to 90° C. After reacting for 16 hr, the reaction bottle was cooled to room temperature, and a substantial amount of ethyl ether was added into the reaction bottle. After stirring for 1 hr and then standing, the precipitate was gathered. Next, the precipitate was dried in a vacuum oven at 80° C. Next, the result was extracted using dichloromethane as the extraction solvent, obtaining the modified polyvinyl alcohol (8) (having the repeating unit A

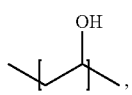

repeating unit B

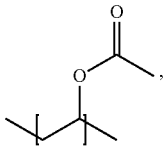

and repeating unit C

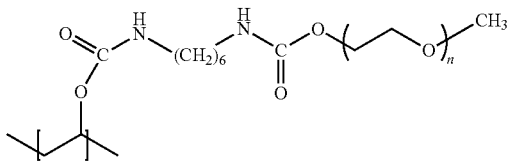

(n>1, and the moiety

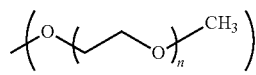

having a weight average molecular weight of about 5000), wherein the repeating units A, B, and C are arranged in a random fashion).

TABLE 2

|  | methoxy polyethylene glycol weight average molecular weight | esterification degree 20% of polyvinyl acetate (g) | methoxy polyethylene glycol (g) | HDI (mL) | solvent (mL) |
|---|---|---|---|---|---|
| modified polyvinyl alcohol (1) | 1900 | 15.8 | 57 | 4.5 | 170/DMSO |
| modified polyvinyl alcohol (2) | 1900 | 86.2 | 250 | 19 | 713/DMSO |

TABLE 2-continued

|  | methoxy polyethylene glycol weight average molecular weight | esterification degree 20% of polyvinyl acetate (g) | methoxy polyethylene glycol (g) | HDI (mL) | solvent (mL) |
|---|---|---|---|---|---|
| modified polyvinyl alcohol (3) | 1900 | 137.9 | 200 | 17.2 | 716/DMSO |
| modified polyvinyl alcohol (4) | 1900 | 46 | 200 | 15.7 | 611/DMSO |
| modified polyvinyl alcohol (5) | 1900 | 124.1 | 180 | 13.6 | 847/DMAc |
| modified polyvinyl alcohol (6) | 1900 | 137.9 | 200 | 17.2 | 716/DMAc |
| modified polyvinyl alcohol (7) | 2000 | 86.2 | 263 | 19 | 740/DMSO |
| modified polyvinyl alcohol (8) | 5000 | 78.6 | 150 | 4.33 | 485/DMSO |

Next, $^1$H-NMR spectra of modified polyvinyl alcohol (1)-(8) were measured, and the methoxy polyethylene glycol grafting ratio was determined (according to the equivalent ratio between the repeating unit C and all repeating units (i.e. repeating units A, B, and C) and shown in Table 3. The equivalents of repeating units A, B, and C were determined by measuring the hydrogen signal area integration (the signal ($\delta$=1.2-1.8) was —CH$_2$ peak of repeating units A, B, and C; the signal ($\delta$=1.8-2.0) was —CH$_3$ peak of repeating unit B; the signal ($\delta$=3.23) was —CH$_3$ peak of repeating unit C; the signal ($\delta$=3.55-4.1) was —CH peak of repeating unit A; and the signal ($\delta$=4.2-5.2) was —OH peak of repeating unit A and —CH peak of repeating unit B). The weight percentages of repeating units A, B, and C are shown in Table 3. The weight percentages of repeating units A, B, and C were measured via the methoxy polyethylene glycol grafting ratio (according to the area integrations of —CH$_3$ peak of repeating unit C) and the weight average molecular weight of the modified polyvinyl alcohol.

TABLE 3

|  | weight percentage of repeating unit A (wt %) | weight percentage of repeating unit B (wt %) | weight percentage of repeating unit C (wt %) | methoxy polyethylene glycol moiety grafting ratio (%) |
|---|---|---|---|---|
| modified polyvinyl alcohol (1) | 22 | 12 | 66 | 4.6 |
| modified polyvinyl alcohol (2) | 24 | 12 | 64 | 4.2 |
| modified polyvinyl alcohol (3) | 39 | 20 | 41 | 1.7 |
| modified polyvinyl alcohol (4) | 20 | 10 | 70 | 5.4 |
| modified polyvinyl alcohol (5) | 39 | 20 | 41 | 1.7 |

TABLE 3-continued

| | weight percentage of repeating unit A (wt %) | weight percentage of repeating unit B (wt %) | weight percentage of repeating unit C (wt %) | methoxy polyethylene glycol moiety grafting ratio (%) |
|---|---|---|---|---|
| modified polyvinyl alcohol (6) | 41 | 21 | 38 | 1.5 |
| modified polyvinyl alcohol (7) | 24 | 12 | 64 | 4.0 |
| modified polyvinyl alcohol (8) | 48 | 24 | 29 | 0.4 |

EXAMPLE 9

The modified polyvinyl alcohol (1) was further subjected to an esterification in the following steps: 60 g of modified polyvinyl alcohol (1) (prepared by Example 1) and 470 mL of dimethylacetamide (DMAC) were added into a reaction bottle. Next, the reaction bottle was stirred and heated to 80° C. for 2 hr. After the modified polyvinyl alcohol (1) dissolving in dimethylacetamide (DMAC) uniformly, the reaction bottle was cooled to 30-35, and then 0.51 g of 4-dimethylaminopyridine (DMAP) was added into the reaction bottle. After stirring for 10 min, the reaction bottle was placed in a water bath tank at room temperature, and then 7.9 mL of acetic anhydride was added into the reaction bottle slowly. After the addition of acetic anhydride was complete, 12.8 mL of triethylamine was added into the reaction bottle at room temperature. After stirring at 40° C. for 16 hr, the reaction bottle was cooled to room temperature, and then a substantial amount of ethyl ether was added into the reaction bottle. After stirring for 1 hr and then standing, the precipitate was gathered. Next, the precipitate was dried in a vacuum oven at 80° C. Next, the result was subjected to a dialysis purification, obtaining the modified polyvinyl alcohol (9) (having the repeating unit A

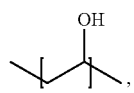

repeating unit B

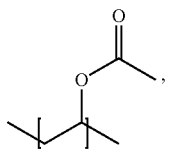

and repeating unit C

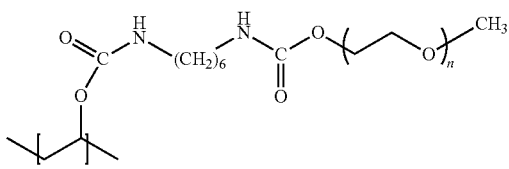

(n>1, and the moiety

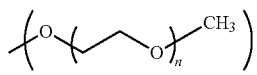

having a weight average molecular weight of about 1900), wherein the repeating units A, B, and C are arranged in a random fashion). The amounts of components of the above esterification are shown in Table 4.

EXAMPLE 10

The modified polyvinyl alcohol (2) was further subjected to an esterification in the following steps: 60 g of modified polyvinyl alcohol (2) (prepared by Example 1) and 741 mL of dimethylacetamide (DMAC) were added into a reaction bottle. Next, the reaction bottle was stirred and heated to 80° C. for 2 hr. After the modified polyvinyl alcohol (1) dissolving in dimethylacetamide (DMAC) uniformly, the reaction bottle was cooled to 30-35, and then 1.3 g of 4-dimethylaminopyridine (DMAP) was added into the reaction bottle. After stirring for 10 min, the reaction bottle was placed in a water bath tank at room temperature, and then 20.0 mL of acetic anhydride was added into the reaction bottle slowly. After the addition of acetic anhydride was complete, 32.5 mL of triethylamine was added into the reaction bottle at room temperature. After stirring at 40° C. for 16 hr, the reaction bottle was cooled to room temperature, and then a substantial amount of ethyl ether was added into the reaction bottle. After stirring for 1 hr and then standing, the precipitate was gathered. Next, the precipitate was dried in a vacuum oven at 80° C. Next, the result was subjected to a dialysis purification, obtaining the modified polyvinyl alcohol (10) (having the repeating unit A

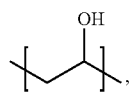

repeating unit B

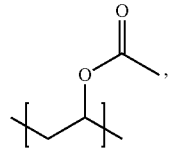

and repeating unit C

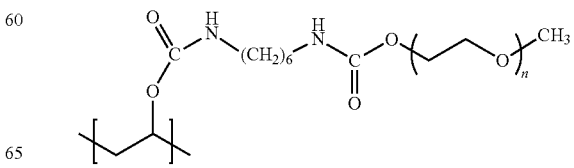

(n>1, and the moiety

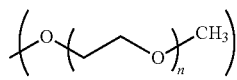

having a weight average molecular weight of about 1900), wherein the repeating units A, B, and C are arranged in a random fashion). The amounts of components of the above esterification are shown in Table 4.

EXAMPLE 11

The modified polyvinyl alcohol (2) was further subjected to an esterification in the following steps: 60 g of modified polyvinyl alcohol (2) (prepared by Example 1) and 912 mL of dimethylacetamide (DMAC) were added into a reaction bottle. Next, the reaction bottle was stirred and heated to 80° C. for 2 hr. After the modified polyvinyl alcohol (1) dissolving in dimethylacetamide (DMAC) uniformly, the reaction bottle was cooled to 30-35, and then 1.94 g of 4-dimethylaminopyridine (DMAP) was added into the reaction bottle. After stirring for 10 min, the reaction bottle was placed in a water bath tank at room temperature, and then 30.0 mL of acetic anhydride was added into the reaction bottle slowly. After the addition of acetic anhydride was complete, 48.7 mL of triethylamine was added into the reaction bottle at room temperature. After stirring at 40° C. for 16 hr, the reaction bottle was cooled to room temperature, and then a substantial amount of ethyl ether was added into the reaction bottle. After stirring for 1 hr and then standing, the precipitate was gathered. Next, the precipitate was dried in a vacuum oven at 80° C. Next, the result was subjected to a dialysis purification, obtaining the modified polyvinyl alcohol (11) (having the repeating unit A

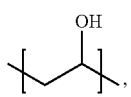

repeating unit B

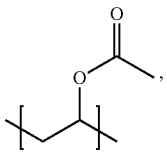

and repeating unit C

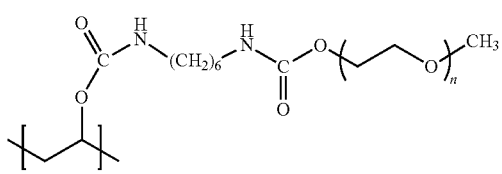

(n>1, and the moiety

having a weight average molecular weight of about 1900), wherein the repeating units A, B, and C are arranged in a random fashion). The amounts of components of the above esterification are shown in Table 4.

TABLE 4

|  | modified polyvinyl alcohol (g) | acetic anhydride (mL) | 4-dimethyl-amino-pyridine (g) | triethyl-amine (mL) | dimethyl-acetamide (DMAC) (mL) |
|---|---|---|---|---|---|
| modified polyvinyl alcohol (9) | modified polyvinyl alcohol (1)/60 g | 7.9 | 0.51 | 12.8 | 470 |
| modified polyvinyl alcohol (10) | modified polyvinyl alcohol (2)/60 g | 20 | 1.3 | 32.5 | 741 |
| modified polyvinyl alcohol (11) | modified polyvinyl alcohol (2)/60 g | 30 | 1.94 | 48.7 | 912 |

Next, $^1$H-NMR spectra of modified polyvinyl alcohol (9)-(11) were measured, and the esterification degrees of modified polyvinyl alcohol (9)-(11) were determined (according to the equivalent ratio between the repeating unit B and all repeating units (i.e. repeating units A, B, and C) and shown in Table 5. The equivalents of repeating units A, B, and C were determined by measuring the hydrogen signal area integration (the signal ($\delta$=1.2-1.8) was —CH$_2$ peak of repeating units A, B, and C; the signal ($\delta$=1.8-2.0) was —CH$_3$ peak of repeating unit B; the signal ($\delta$=3.2) was —CH$_3$ peak of repeating unit C.

The hydrophilic moiety grafting ratio was determined via the hydrogen signal ($\delta$=3.2) area integration of repeating unit C, and the esterification degree of the modified polyvinyl alcohol was determined via the hydrogen signal ($\delta$=1.8-2.0) area integration of repeating unit B. The weight percentages of repeating units A, B, and C are shown in Table 5. The weight percentages of repeating units A, B, and C were measured via the hydrophilic moiety grafting ratio, esterification degree, and the weight average molecular weight of the modified polyvinyl alcohol (9)-(11).

TABLE 5

|  | weight percentage of repeating unit A (wt %) | weight percentage of repeating unit B (wt %) | weight percentage of repeating unit C (wt %) | esterification degree (%) |
|---|---|---|---|---|
| modified polyvinyl alcohol (9) | 15 | 22 | 62 | 40 |
| modified polyvinyl alcohol (10) | 12 | 40 | 49 | 61 |
| modified polyvinyl alcohol (11) | 5 | 52 | 43 | 82 |

EXAMPLE 12

The hydrophobic moiety was introduced into the modified polyvinyl alcohol (3) by following steps: 50 g of modified polyvinyl alcohol (3) (prepared from Example 3) and 256 mL of dimethyl sulfoxide (DMSO) were added into a reaction bottle. Next, the reaction bottle was heated to 100° C. and then stirred for 2 hr, resulting in the modified polyvinyl alcohol (3) being dissolved into DMSO uniformly. Next, the reaction bottle was cooled to room temperature, and then 6.2 mL of phenyl isocyanate was added into the reaction bottle. After stirring, the reaction bottle was heated to 90° C. for 22 hr. Next, the result was subjected to a precipitation purification (with ethyl ether) and a dialysis purification, obtaining the modified polyvinyl alcohol (12) (having the repeating unit A

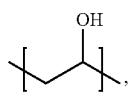

repeating unit B

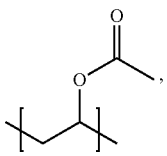

repeating unit C

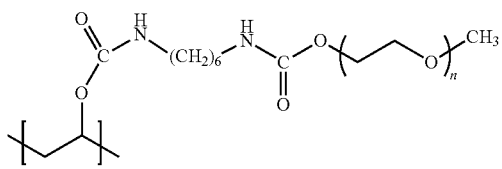

(n>1, and the moiety

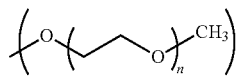

having a weight average molecular weight of about 1900), and repeating unit D

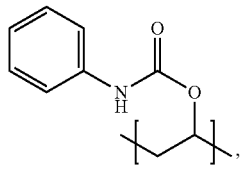

wherein the repeating units A, B, C, and D are arranged in a random fashion). The amounts of components of the above esterification are shown in Table 6.

EXAMPLE 13

The hydrophobic moiety was introduced into the modified polyvinyl alcohol (3) by following steps: 50 g of modified polyvinyl alcohol (3) (prepared from Example 3) and 257 mL of dimethyl sulfoxide (DMSO) were added into a reaction bottle. Next, the reaction bottle was heated to 100° C. and then stirred for 2 hr, resulting in the modified polyvinyl alcohol (3) being dissolved into DMSO uniformly. Next, the reaction bottle was cooled to room temperature, and then 8.2 mL of naphthyl isocyanate was added into the reaction bottle. After stirring, the reaction bottle was heated to 90° C. for 22 hr. Next, the result was subjected to a precipitation purification (with ethyl ether) and a dialysis purification, obtaining the modified polyvinyl alcohol (13) (having the repeating unit A

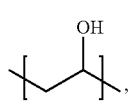

repeating unit B

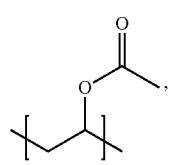

repeating unit C

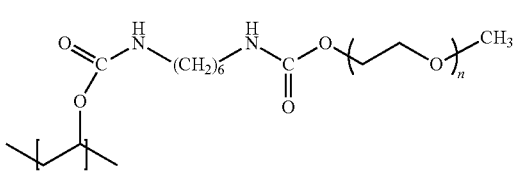

(n>1, and the moiety

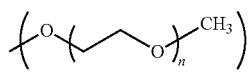

having a weight average molecular weight of about 1900), and repeating unit D

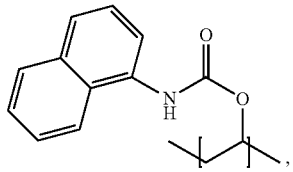

wherein the repeating units A, B, C, and D are arranged in a random fashion). The amounts of components of the above esterification are shown in Table 6.

TABLE 6

| | modified polyvinyl alcohol | aryl isocyanate | dimethyl sulfoxide (mL) |
|---|---|---|---|
| modified polyvinyl alcohol (12) | modified polyvinyl alcohol (4)/50 g | phenyl isocyanate/ 6.2 mL | 256 |
| modified polyvinyl alcohol (13) | modified polyvinyl alcohol (4)/50 g | naphthyl isocyanate/ 8.2 mL | 257 |

Next, $^1$H-NMR spectra of modified polyvinyl alcohol (12)-(13) were measured, and the hydrophobic moiety (i.e. N-phenyl isocyanate group, or N-naphthyl isocyanate group) grafting ratio of modified polyvinyl alcohol (12)-(13) were determined (according to the equivalent ratio between the repeating unit D and all repeating units (i.e. repeating units A, B, C, and D) and shown in Table 7). The equivalents of repeating units A, B, C, and D were determined by measuring the hydrogen signal area integration (the signal ($\delta$=1.2-1.8) was —CH$_2$ peak of repeating units A, B, and C; the signal ($\delta$=1.8-2.0) was —CH$_3$ peak of repeating unit B; the signal ($\delta$=3.23) was —CH$_3$ peak of repeating unit C; the signal ($\delta$=3.55-4.1) was —CH peak of repeating unit A; the signal ($\delta$=4.2-5.2) was —OH peak of repeating unit A and —CH peak of repeating unit B; and the signal ($\delta$=7.0-8.5) was hydrogen peak of aryl group of repeating unit D. The weight percentages of repeating units A, B, C, and D are shown in Table 7. The weight percentages of repeating units A, B, C, and D were measured via the hydrophilic moiety grafting ratio, esterification degree, hydrophobic moiety grafting ratio, and the weight average molecular weight of the modified polyvinyl alcohol (12)-(13).

TABLE 7

| | weight percentage of repeating unit A (wt %) | weight percentage of repeating unit B (wt %) | weight percentage of repeating unit C (wt %) | weight percentage of repeating unit D (wt %) | hydrophobic moiety grafting ratio (%) |
|---|---|---|---|---|---|
| modified polyvinyl alcohol (12) | 31 | 18 | 36 | 15 | 9 |
| modified polyvinyl alcohol (13) | 33 | 18 | 36 | 13 | 6 |

EXAMPLE 14

Methoxy polyethylene glycol prepolymer (4) (prepared according to Preparation Example 7, and the components for preparing the Methoxy polyethylene glycol prepolymer (4) including 200.0 g of methoxy polyethylene glycol (with a weight average Molecular weight of 1900), 23.7 g of methylene diphenyl diisocyanate (MDI), 68.9 g of polyvinyl acetate (PVAc) (with an esterification degree of 20%, and a weight average molecular weight of about 10,000-12,000), and 620 mL of dimethyl sulfoxide (DMSO) were added into a reaction bottle. After stirring uniformly, the reaction bottle was heated to 60° C.

After reacting for 16 hr, the reaction bottle was cooled to room temperature, and a substantial amount of ethyl ether was added into the reaction bottle. After stirring for 1 hr and then standing, the precipitate was gathered. Next, the precipitate was dried in a vacuum oven at 80° C. Next, the result was purified by ultrafilitration, obtaining the modified polyvinyl alcohol (14) (having the repeating unit A

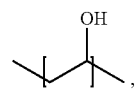

repeating unit B

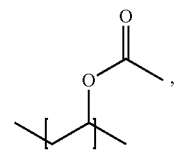

and repeating unit C

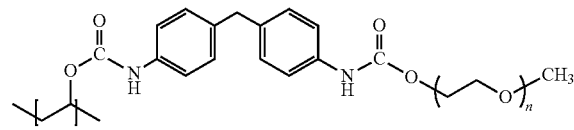

(n>1, and the moiety

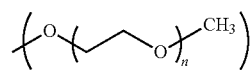

having a weight average molecular weight of about 1900), wherein the repeating units A, B, and C are arranged in a random fashion).

Next, $^1$H-NMR spectrum of modified polyvinyl alcohol (14) was measured, and the esterification degree of modified polyvinyl alcohol (14) were determined (according to the equivalent ratio between the repeating unit B and all repeating units (i.e. repeating units A, B, and C) and shown in Table 8.

The equivalents of repeating units A, B, and C were determined by measuring the hydrogen signal area integration (the signal ($\delta$=1.2-1.8) was —CH$_2$ peak of repeating units A, B, and C; the signal ($\delta$=1.8-2.0) was —CH$_3$ peak of repeating unit B; the signal ($\delta$=3.3) was —CH$_3$ peak of repeating unit C. The weight percentages of repeating units A, B, and C are shown in Table 8. The hydrophilic moiety grafting ratio of the modified polyvinyl alcohol was determined via the hydrogen signal ($\delta$=3.2) area integration of repeating unit C, and the esterification degree of the modified polyvinyl alcohol was determined via the hydrogen signal ($\delta$=1.8-2.0) area integration of repeating unit B. The weight percentages of repeating units A, B, and C were measured via the hydrophilic moiety grafting ratio, esterification degree, and the weight average molecular weight of the modified polyvinyl alcohol (14).

TABLE 8

|  | weight percentage of repeating unit A (wt %) | weight percentage of repeating unit B (wt %) | weight percentage of repeating unit C (wt %) | methoxy polyethylene glycol moiety grafting ratio (%) |
|---|---|---|---|---|
| modified polyvinyl alcohol (14) | 45 | 22 | 33 | 1.2 |

Analysis for Modified Polyvinyl Alcohol: Critical Micelle Concentration (CMC)

EXAMPLE 15

The critical micelle concentration of the modified polyvinyl alcohol was determined. The testing methods are described in the following: First, pyrene was dissolved into acetone to prepare a pyrene-containing acetone solution ($1.8 \times 10^{-4}$ M). The modified polyvinyl alcohol (2)-(3), and (9)-(11) were separately formulated to 2 mg/mL aqueous solutions. The aqueous solutions (containing the modified polyvinyl alcohol) were then aliquoted to obtain 15 concentrations until the concentration reached $6 \times 10^{-5}$ mg/ml. Each of the aliquots (5 mL) was uniformly mixed with 15 µl of pyrene-containing acetone solution ($1.8 \times 10^{-4}$ M). The mixtures were left to stand in the dark for 16 hours and then the acetone was evaporated under vacuum. Subsequently, each aliquot was analyzed by a fluorescence spectrometer, emission was detected at wavelength 339 nm and an exciting wavelength of excitation spectrum was scanned from 360 to 500 nm. The wavelengths which showed the strongest absorption were recorded. According to the log of the concentration and the absorption on the fluorescence spectra, the point at which the absorption started changing indicated the critical micelle concentration. Table 9 shows the critical micelle concentration (CMC) of several micelle materials.

TABLE 9

|  | Critical micelle concentration (mg/mL) |
|---|---|
| modified polyvinyl alcohol (2) | 0.38 |
| modified polyvinyl alcohol (3) | 0.31 |
| modified polyvinyl alcohol (9) | 0.49 |
| modified polyvinyl alcohol (10) | 0.16 |
| modified polyvinyl alcohol (11) | 0.10 |

As shown in Table 9, the modified polyvinyl alcohol polymer prepared by the Examples of the disclosure has the ability for appearing a micelle structure. The core of the micelle structure constituted by the hydrophobic groups of the modified polyvinyl alcohol polymer can stably carry the hydrophobic drugs.

Solubility

EXAMPLE 16

The modified polyvinyl alcohol (1)-(3), (5), (7)-(8), and (10)-(13) of Examples 1-3, 5, 7-8, and 10-13 of the disclosure were added into various solvent (such as DI water, ethanol (EtOH), dichloromethane (DCM), and dimethyl sulfoxide (DMSO)), to prepare a 10 wt % solution. The dissolution profile of the modified polyvinyl alcohol was observed, and the results are shown in Table 10.

TABLE 10

|  | Solubility (10 wt %) | | | |
|---|---|---|---|---|
|  | DI water | DMSO | ethanol | DCM |
| modified polyvinyl alcohol (1) | soluble | soluble | insoluble | insoluble |
| modified polyvinyl alcohol (2) | soluble | soluble | insoluble | insoluble |
| modified polyvinyl alcohol (3) | soluble | soluble | insoluble | insoluble |
| modified polyvinyl alcohol (5) | soluble | soluble | insoluble | insoluble |
| modified polyvinyl alcohol (7) | soluble | soluble | insoluble | insoluble |
| modified polyvinyl alcohol (8) | soluble | soluble | insoluble | insoluble |
| modified polyvinyl alcohol (9) | soluble | soluble | soluble | slightly soluble |
| modified polyvinyl alcohol (10) | soluble | soluble | soluble | soluble |
| modified polyvinyl alcohol (11) | soluble | soluble | soluble | soluble |
| modified polyvinyl alcohol (12) | soluble | soluble | insoluble | insoluble |
| modified polyvinyl alcohol (13) | slightly soluble | soluble | insoluble | insoluble |

As shown in Table 10, all the modified polyvinyl alcohol polymers of the disclosure are soluble in water, thereby promoting the release of drug. When the modified polyvinyl alcohol polymer has high esterification degree, the modified polyvinyl alcohol polymer has increased solubility in ethanol and dichloromethane. Further, when the hydrophobic moiety is introduce into the modified polyvinyl alcohol polymer, the modified polyvinyl alcohol polymer has reduced solubility in water.

EXAMPLE 17

The modified polyvinyl alcohol (5) prepared from Example 5, commercially available polyvinyl alcohol polymer (with trade No. kollicoat IR, sold and manufactured by BASF), and polyvinyl acetate (PVAc) (with an esterification degree of 20% and a weight average molecular weight of about 10,000-12,000) were added into DI water, and the dissolution profile of the modified polyvinyl alcohol were observed. The modified polyvinyl alcohol (5) of the disclosure was completely dissolved in water, obtaining a clarified liquid. The commercially available polyvinyl alcohol polymer (kollicoat IR) was partially dissolved in water; and, polyvinyl acetate (PVAc) (with an esterification degree of 20% and a weight average molecular weight of about 10,000-12,000) had a relatively low solubility in water. The results are shown in Table 11.

TABLE 11

|  | dissolution time (1 mg/1 mL) | Saturation concentration (in 5 mL H$_2$O) |
|---|---|---|
| modified polyvinyl alcohol (5) | 30 s | >325 mg |
| kollicoat IR | 120 s | 125 mg |
| polyvinyl acetate (with an esterification degree of 20%) | >10 min | <100 mg |

As shown in Table 11, in comparison with kollicoat IR and polyvinyl acetate (with an esterification degree of 20%), the modified polyvinyl alcohol (5) has a relatively high dissolution rate. Therefore, it is expected that the modified polyvinyl alcohol has a relatively high disintegration rate and rapid onset of action in the aqueous environment of the human gastrointestinal tract. Furthermore, due to the relatively high saturation concentration in comparison with kollicoat IR and polyvinyl acetate (with an esterification degree of 20%), the modified polyvinyl alcohol (5) exhibits an improved hydrophilic characteristic. As a result, a relatively high add-on amount of modified polyvinyl alcohol (5) serving as excipient can be still dissolved in the aqueous environment of human gastrointestinal tract.

Thermal Stability

EXAMPLE 18

The modified polyvinyl alcohol (2), (9), (10) and (11) prepared by Examples of the disclosure were analyzed by the differential scanning calorimeter (DSC) and thermogravimetric analyzer (TGA) to determine the temperature of weight loss at 5% and the thermal degradation temperature (Td). The results are shown in Table 12.

TABLE 12

|  | temperature of weight loss at 5% (° C.) | thermal degradation temperature (° C.) |
|---|---|---|
| modified polyvinyl alcohol (2) | 285 | 321 (29%) 430 (66%) |
| modified polyvinyl alcohol (9) | 290 | 330 (33%) 434 (62%) |
| modified polyvinyl alcohol (10) | 308.25 | 331 (43%) 421(53%) |
| modified polyvinyl alcohol (11) | 312.03 | 337 (44%) 422 (52%) |

As shown in Table 12, the thermal degradation temperature and melting point of the modified polyvinyl alcohol polymer of the disclosure is higher than the room temperature (25° C.). It means that the modified polyvinyl alcohol polymer of the disclosure exhibit high thermal stability.

Pelletizability

EXAMPLE 19

The modified polyvinyl alcohol (1)-(3), and (9) prepared from Examples 1-3, and 9 (serving as an excipient) and commercially available excipient (with a trade No. Kollidon® VA64, sold and manufactured by BASF) were individually mixed with fenofibrate (active pharmaceutical ingredient with low solubility in water). The tablet of the mixture (with 4 wt % excipient) was produced by tableting. Next, the tablets were disposed into a disintegration tester, and the disintegration time of the tablet was measured to determine the pelletizability of the excipient. The result was shown in FIG. 1. As shown in FIG. 1, the disintegration time of the Kollidon® VA64 is 13.8 min. The disintegration time of the modified polyvinyl alcohol polymer of the disclosure was 1.5-5 times greater than that of Kollidon® VA64. It means that the modified polyvinyl alcohol of the disclosure exhibits high pelletizability, especially the modified polyvinyl alcohol (2).

Solubility

EXAMPLE 20

The modified polyvinyl alcohol (2), (3)-(5), and (8)-(12) prepared from Examples 2, 3-5, 8, and 9-12 (serving as an excipient), commercially available excipient (with a trade No. Kollidon® VA64, sold and manufactured by BASF), and hydroxypropyl methyl cellulose acetate succinate (HPMC-AS) were individually mixed with API (such as fenofibrate, aprepitant, nevirapine, glyburide, sorafenib, vemurafenib, and telaprevir), where in the weight ratio between the active ingredient and the excipient was 1:10. The mixture was dissolved in water at 25° C., and then the result was stirred by ultrasonic vibration, thereby achieving a balanced state. Next, the amount of the API of the solution was determined by HPLC-UV. The peak area of the API was integrated, and the results are shown in Table 13.

TABLE 13

|  | fenofibrate | aprepitant | nevirapine | glyburide | sorafenib | vemurafenib | telaprevir |
|---|---|---|---|---|---|---|---|
| modified polyvinyl alcohol (2) | 17967 | 41970 | 2014715 | 236939 | ND* | ND | ND |
| modified polyvinyl alcohol (3) | ND | ND | 767947 | 221127 | ND | ND | ND |
| modified polyvinyl alcohol (4) | ND | 18262 | 40813 | ND | 40813 | 53649 | ND |
| modified polyvinyl alcohol (5) | 6706 | 0 | 283184 | 171559 | ND | 36508 | ND |

TABLE 13-continued

|  | fenofibrate | aprepitant | nevirapine | glyburide | sorafenib | vemurafenib | telaprevir |
| --- | --- | --- | --- | --- | --- | --- | --- |
| modified polyvinyl alcohol (8) | ND | ND | 19439 | 38991 | ND | 34087 | ND |
| modified polyvinyl alcohol (9) | 27802 | 52438 | 1061727 | 185387 | ND | ND | ND |
| modified polyvinyl alcohol (10) | 160654 | 68473 | 344937 | 21019 | 116006 | 384734 | 6236 |
| modified polyvinyl alcohol (11) | 181767 | 221752 | 116006 | 84357 | 344937 | 1005170 | 8283 |
| modified polyvinyl alcohol (12) | ND | 24924 | 1623968 | 202145 | 30844 | 131307 | ND |
| Kollidon ® VA64 | 6674 | ND | 521231 | 18807 | ND | 8783 | ND |
| HPMC-AS | ND | ND | ND | ND | ND | ND | ND |

(ND: not detected)

As shown in Table 13, all the modified polyvinyl alcohol polymers of the disclosure, which are serving as excipient, exhibit high solubility.

Solubility for Solid Dispersion

EXAMPLE 21

Figure 2:
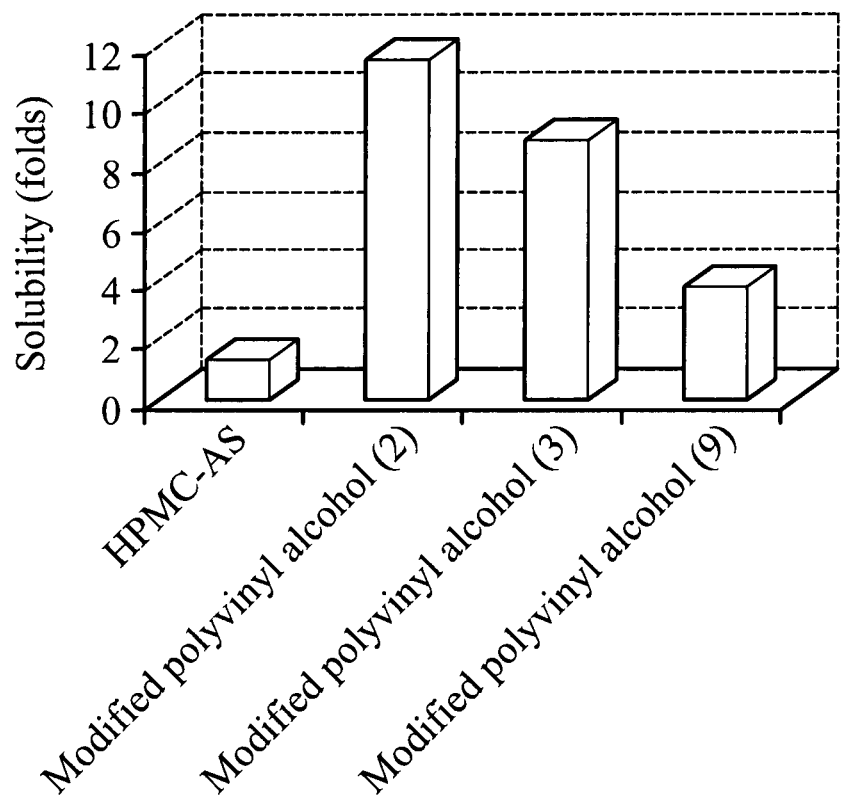

The modified polyvinyl alcohol (2), (3), and (9) prepared from Examples 2, 3, and 9 (serving as an excipient) and hydroxypropyl methyl cellulose acetate succinate (HPMC-AS) were individually mixed with API (such as fenofibrate), wherein the weight ratio between the API and the excipient was 1:2. The mixture was dissolved in methanol, and then subjected to a solid dispersion to form a powder. Next, the powder was dissolved in water at 25° C., and then the result was stirred by ultrasonic vibration, thereby achieving a balanced state. Next, the amount of the API of the solution was determined by HPLC-UV. The peak area of the API was integrated, and the results are shown in FIG. 2 (the peak area of the HPMC-AS as a comparative reference). As shown in FIG. 2, the peak area of the modified polyvinyl alcohol polymer of the disclosure was about 2.5-10 times greater than that of HPMC-AS. It means that the modified polyvinyl alcohol of the disclosure exhibits high solubility for solid dispersion, especially the modified polyvinyl alcohol (2).

Figure 3:
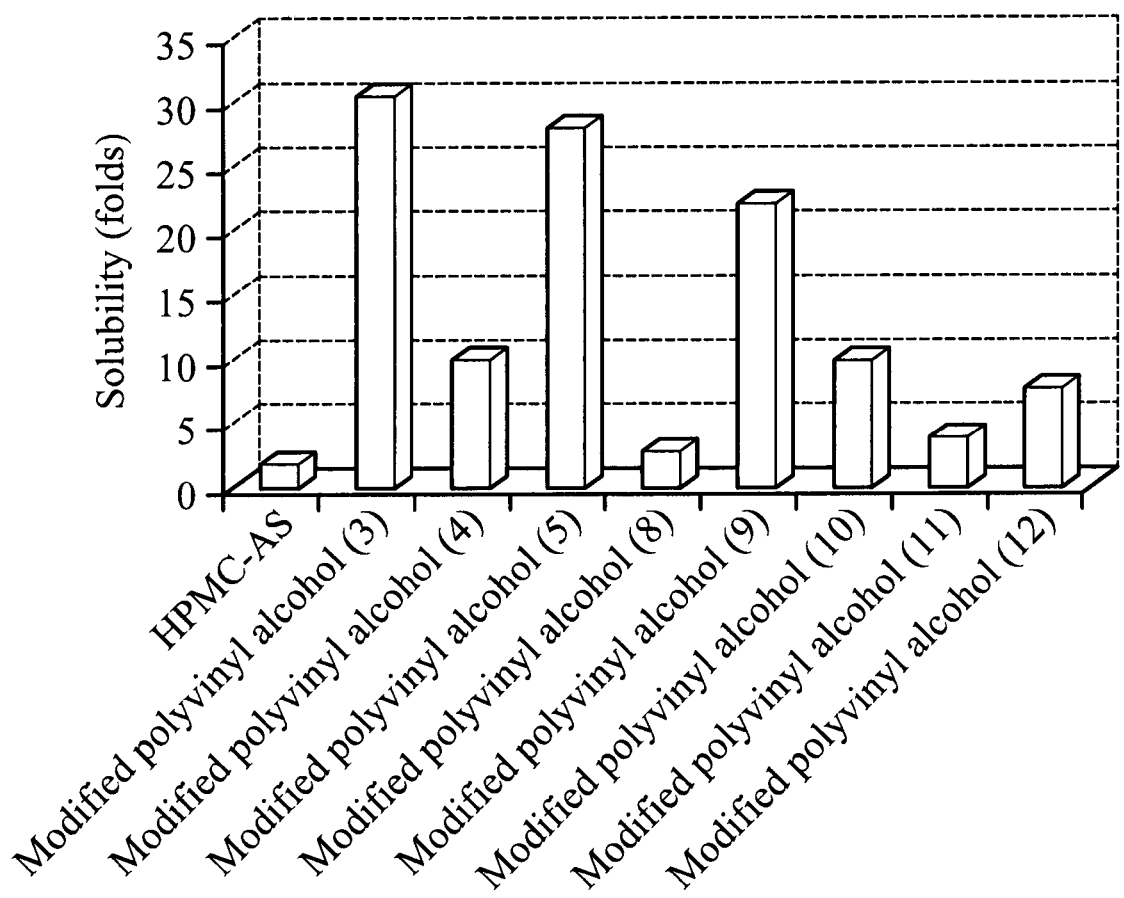

The modified polyvinyl alcohol (3)-(5), (8), and (9)-(12) prepared from Examples 3-5, 8, and 9-12 (serving as an excipient) and hydroxypropyl methyl cellulose acetate succinate (HPMC-AS) were individually mixed with an API (such as aprepitant), wherein the weight ratio between the API and the excipient was 1:1. The mixture was dissolved in methanol, and then subjected to a solid dispersion to form a powder. Next, the powder was dissolved in water at 25° C., and then the result was stirred by ultrasonic vibration, thereby achieving a balanced state. Next, the amount of the API of the solution was determined by HPLC-UV. The peak area of the API was integrated, and the results are shown in FIG. 3 (the peak area of the HPMC-AS as a comparative reference). As shown in FIG. 3, the peak area of the modified polyvinyl alcohol polymer of the disclosure was about 2-30 times greater than that of HPMC-AS. It means that the modified polyvinyl alcohol of the disclosure exhibits high solubility for solid dispersion, especially the modified polyvinyl alcohol (3).

Cell Viability

EXAMPLE 22

Figure 4:
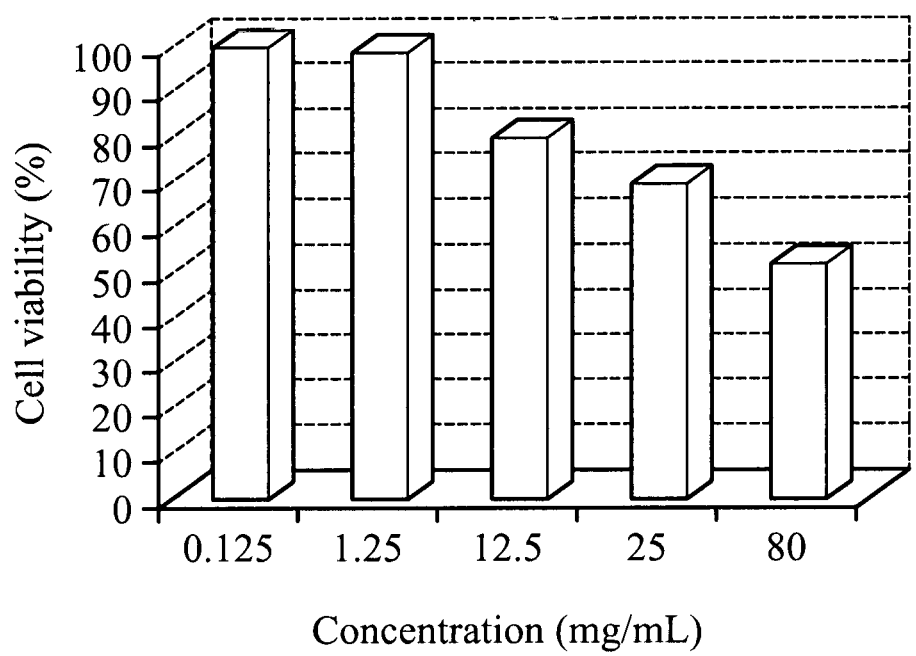
FIG. 4 is a graph plotting the cell viability of the modified polyvinyl alcohol (2) aqueous solution in various concentrations.

The modified polyvinyl alcohol (2) prepared from Example 2 was dissolved in water, obtaining a solution with a concentration of 10 mg/mL. The cytotoxicity of the modified polyvinyl alcohol (2) was measured according to the standard requirements of ISO 10993-5, thereby determining the effect on the cell viability of the modified polyvinyl alcohol. As shown in FIG. 4, the cell viability is reduced when the concentration of the modified polyvinyl alcohol (2) is increased. It results from the increased viscosity due to the high concentration of the modified polyvinyl alcohol, rather than the toxicity of the modified polyvinyl alcohol (2).

Figure 5:
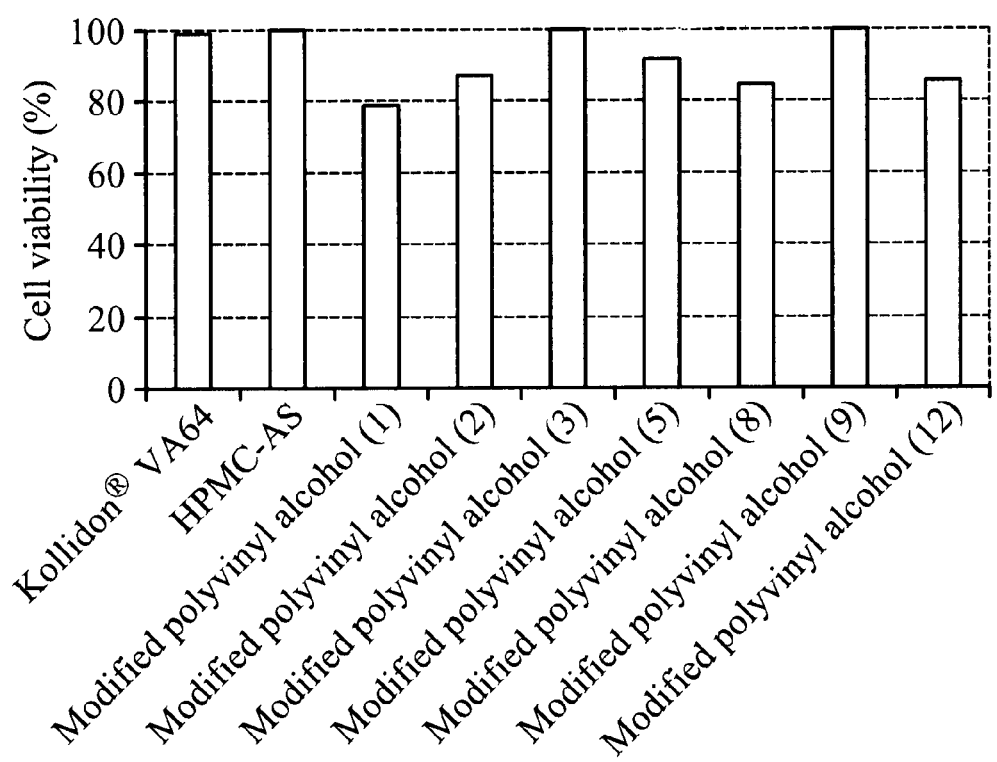

Next, modified polyvinyl alcohol (1)-(3), (5), (8)-(9), and (12) prepared from Example 2, 3-5, 8, and 9-12, commercially available excipient Kollidon® VA64, sold and manufactured by BASF), and hydroxypropyl methyl cellulose acetate succinate (HPMC-AS) were dissolved in water individually, obtaining a solution with a concentration of 10 mg/mL. The cytotoxicity of the above excipient was measured according to the standard requirements of ISO 10993-5, thereby determining the effect on the cell viability of the excipient. As shown in FIG. 5, the cell viabilities of all modified polyvinyl alcohol are larger than 80%. Therefore, the modified polyvinyl alcohol of the disclosure does not cause significant cytotoxicity.

Mutagenicity

EXAMPLE 23

The mutagenicity of modified polyvinyl alcohol (2), (3), (5), (8), (9), and (12) prepared from Example 2, 3, 5, 8, 9, and 12 was determined by the Ames test. The Ames test was carried out using *Sal. Typhimurium* TA98 strain and *Sal. Typhimurium* TA100 strain without an enzyme for activating metabolism of drugs (S9). DMSO (100 μL/plate) was used as negative control, and 4-nitro-o-phenylenediamine (NOPD) (100 μL/plate) was used as positive control. The results are shown in Table 14.

TABLE 14

|  | Concentration (mg/mL) | TA98 (CFU/plate) | TA100 (CFU/plate) |
| --- | --- | --- | --- |
| modified polyvinyl alcohol (2) | 10 | 14 | 142 |
|  | 1 | 14 | 123 |
|  | 0.1 | 12 | 128 |
| modified polyvinyl alcohol (3) | 10 | 17 | 148 |
|  | 1 | 13 | 133 |
|  | 0.1 | 9 | 141 |
| modified polyvinyl alcohol (5) | 10 | 27 | 154 |
|  | 1 | 19 | 118 |
|  | 0.1 | 17 | 117 |
| modified polyvinyl alcohol (8) | 10 | 26 | 134 |
|  | 1 | 13 | 105 |
|  | 0.1 | 15 | 127 |
| modified polyvinyl alcohol (9) | 10 | 16 | 144 |
|  | 1 | 16 | 130 |
|  | 0.1 | 12 | 111 |
| modified polyvinyl alcohol (12) | 10 | 30 | 143 |
|  | 1 | 29 | 123 |
|  | 0.1 | 26 | 111 |
| Negative control (DMSO) | 100 µL/plate | 17 | 106 |
| Positive control (NOPD) | 100 µL/plate | 1200 | 1019 |

The mutagenicity of modified polyvinyl alcohol (2), (5), (8), (9), and (12) prepared from Example 2, 5, 8, 9, and 12 was determined by the Ames test. The Ames test was carried out using *Sal. Typhimurium* TA98 strain and *Sal. Typhimurium* TA100 strain with an enzyme for activating metabolism of drugs (S9). DMSO (100 µL/plate) was used as negative control, and (+)Benzo[α]pyrene (100 µL/plate) was used as positive control. The results are shown in Table 15.

TABLE 15

|  | Concentration (mg/mL) | TA98 (CFU/plate) + S9 | TA100 (CFU/plate) + S9 |
| --- | --- | --- | --- |
| modified polyvinyl alcohol (2) | 10 | 18 | 121 |
|  | 1 | 18 | 105 |
|  | 0.1 | 19 | 107 |
| modified polyvinyl alcohol (5) | 10 | 23 | 118 |
|  | 1 | 16 | 100 |
|  | 0.1 | 18 | 97 |
| modified polyvinyl alcohol (8) | 10 | 45 | 167 |
|  | 1 | 48 | 137 |
|  | 0.1 | 43 | 158 |
| modified polyvinyl alcohol (9) | 10 | 28 | 143 |
|  | 1 | 24 | 106 |
|  | 0.1 | 19 | 118 |
| modified polyvinyl alcohol (12) | 10 | 46 | 162 |
|  | 1 | 37 | 165 |
|  | 0.1 | 47 | 157 |
| Negative control (DMSO) | 100 µL/plate | 34 | 134 |
| Positive control ((+)Benzo[α]pyrene) | 100 µL/plate | 151 | 290 |

As shown in Tables 14 and 15, the number of surviving colonies (per plate) of the modified polyvinyl alcohol is within the normal range (i.e. the number of surviving colonies is less than two times of the number of spontaneous surviving colonies. Therefore, the modified polyvinyl alcohol of the disclosure within the specific concentration is non-mutagenic to *Sal. Typhimurium* TA98 strain and *Sal. Typhimurium* TA100 strain, with or without the presence of enzyme for activating metabolism of drugs (S9). Accordingly, due to the solubility, the polymer of the disclosure can serve as an excipient for improving the absorption, and dissolution of the compounds classified as BCS Class II within the human body. As a result, the bio-availability of the drugs can be enhanced by means of the polymer, without changing the dosage form of the drugs.

On the other hand, besides the solubility, the polymer of the disclosure has the functions for disintegrating and/or bonding the pharmaceutical composition. Therefore, the amount of the additional excipient used in a solid dosage form of the pharmaceutical composition can be reduced, resulting in the reduction of side reaction of drugs. Moreover, the polymer of the disclosure does not cause significant biotoxicity and mutagenicity.

It will be clear that various modifications and variations can be made to the disclosed methods and materials. It is intended that the specification and examples be considered as exemplary only, with the true scope of the disclosure being indicated by the following claims and their equivalents.

What is claimed is:

1. A polymer, comprising a first repeating unit, a second repeating unit, and a third repeating unit, wherein the first repeating unit is

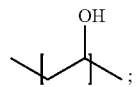

the second repeating unit is

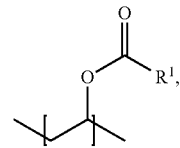

wherein $R^1$ is $C_{1-6}$ alkyl group; and, the third repeating unit is

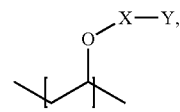

wherein X is

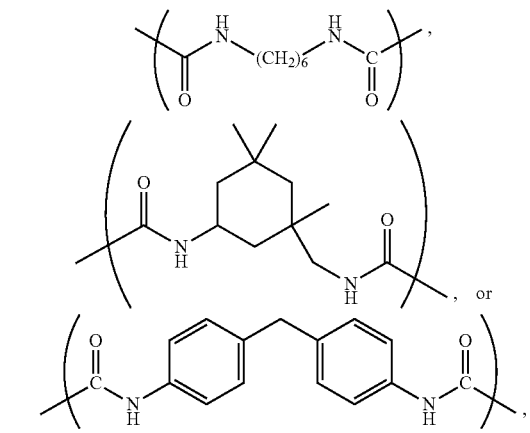

and Y is hydrophilic polymeric moiety, wherein the hydrophilic polymeric moiety is polyethylene glycol moiety, methoxy polyethylene glycol moiety, polyvinylpyrrolidone moiety, polyacrylic acid moiety, or polymethacrylic acid moiety, wherein the first repeating unit has a weight percentage of 5-50 wt %, the second repeating unit has a weight percentage between 10-55 wt %, and the third repeating unit has a weight percentage between 25-75 wt %, based on the total weight of the first repeating unit, the second repeating unit, and the third repeating unit, wherein the hydrophilic polymeric moiety has a grafting ratio between 0.1% and 10%.

2. The polymer as claimed in claim 1, wherein the hydrophilic polymeric moiety has a weight average molecular weight between 500 and 100,000.

3. The polymer as claimed in claim 1, wherein the third repeating unit is

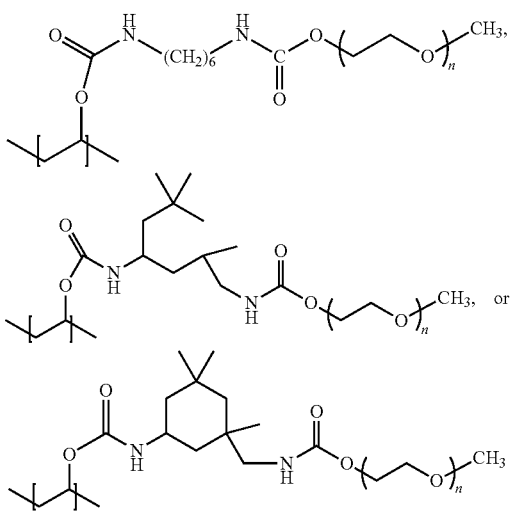

wherein n>1.

4. The polymer as claimed in claim 1, wherein the third repeating unit is

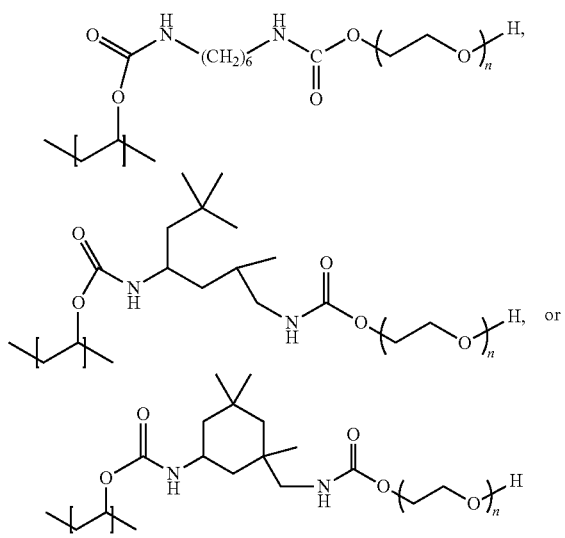

wherein n>1.

5. The polymer as claimed in claim 1, wherein $R^1$ is methyl group, ethyl group, propyl group, isopropyl group, butyl group, isobutyl group, tert-butyl group, pentyl group, or hexyl group.

6. The polymer as claimed in claim 1, wherein the polymer has a weight average molecular weight between 5,000 and 500,000.

7. The polymer as claimed in claim 1, wherein the second repeating unit is

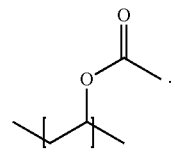

8. The polymer as claimed in claim 7, wherein the polymer has an esterification degree between 10% and 85%.

9. The polymer as claimed in claim 1, further comprising: a fourth repeating unit, wherein the fourth repeating unit is

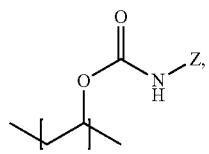

wherein Z is a hydrophobic moiety.

10. The polymer as claimed in claim 9, wherein the hydrophobic moiety is phenyl group, naphthyl group, or $C_{4-20}$ alkyl group.

11. The polymer as claimed in claim 9, wherein the hydrophobic moiety is a polyester moiety.

12. The polymer as claimed in claim 11, wherein the polyester moiety has a weight average molecular weight between 500 and 5,000.

13. The polymer as claimed in claim 11, wherein the polyester moiety is polycaprolactone moiety, polylactic acid moiety, polyglycolic acid moiety, or poly(lactic-co-glycolic) acid moiety.

14. The polymer as claimed in claim 9, wherein the first repeating unit has a weight percentage of 5-40 wt %, the second repeating unit has a weight percentage of 10-50 wt %, the third repeating unit has a weight percentage of 25-70 wt %, and the fourth repeating unit has a weight percentage of 5-50 wt %, based on the total weight of the first repeating unit, the second repeating unit, and the third repeating unit.

15. The polymer as claimed in claim 12, wherein the hydrophobic moiety has a grafting ratio between 0.1% and 10%.

16. A pharmaceutical composition, comprising:
a bioactive component; and
an excipient, wherein the excipient comprises the polymer as claimed in claim 1.

17. The pharmaceutical composition as claimed in claim 16, wherein the bioactive component is lipophilic drug.

18. The pharmaceutical composition as claimed in claim 17, wherein the bioactive component is non-steroid anti-inflammatory drug, psychotropic drug, antilipemic drug, antiemetic drug, or a combination thereof.

19. The pharmaceutical composition as claimed in claim 17, wherein the bioactive component is ibuprofen, naproxen, ketoprofen, flurbiprofen, fenoprofen, suprofen, fluprofen, fenbufen, tolmetin sodium, zomepirac, sulindac, indomethacin, mefenamic acid, meclofenamate, diflunisal, flufenisal, piroxicam, sudoxicam, isoxicam, chlorpheniramine, brompheniramine, dexchlorpheniramine, dexbrompheniramine, triprolidine, chlorcyclizine, diphenhydramine, doxylamine, tripelennamine, cyproheptadine, bromodiphenhydramine, phenindamine, pyrilamine, azatadine, acrivastine, astemizole, azelastine, cetirizine, ebastine, fexofenadine, ketotifen, carbinoxamine, desloratadine, loratadine, pheniramine, thonzylamine, mizolastine, terfenadine, chlophendianol, caramiphen, dextromethorphan, codeine, hydrocodone, pseudoephedrine, ephedrine, phenylephrine, guaifenesin, guaiacotsulfonate, celecoxib, rofecoxib, valdecoxib, acetaminophen, phenacetin, acteylsalicylic acid, aripiprazole, fenofibrate, aprepitant, nevirapine, glyburide, sorafenib, vemurafenib, telaprevir, or a combination thereof.

\* \* \* \* \*